United States Patent [19]
Kira

[11] Patent Number: 4,871,361
[45] Date of Patent: Oct. 3, 1989

[54] ARTIFICIAL VESSEL

[75] Inventor: Kazuaki Kira, Kobe, Japan

[73] Assignee: Kanegafuchi Kagaku Kogyo Kabushiki Kaisha, Osaka, Japan

[21] Appl. No.: 55,970

[22] Filed: Jun. 1, 1987

Related U.S. Application Data

[63] Continuation-in-part of Ser. No. 900,052, Aug. 25, 1986, abandoned.

[30] Foreign Application Priority Data

Feb. 26, 1987 [JP] Japan .................................. 62-43713

[51] Int. Cl.$^4$ ............................ A61F 2/06; A01N 1/02
[52] U.S. Cl. ............................................ 623/1; 427/2; 128/334 R
[58] Field of Search ............... 623/1, 12, 66; 264/519; 128/334 R; 427/2

[56] References Cited

U.S. PATENT DOCUMENTS

| | | |
|---|---|---|
| 3,745,203 | 7/1973 | Harper . |
| 3,991,147 | 11/1976 | Knipp et al. . |
| 4,173,689 | 11/1979 | Lyman et al. . |
| 4,208,745 | 6/1980 | Okita . |
| 4,234,535 | 11/1980 | Okita .................................. 264/519 |
| 4,254,180 | 3/1981 | Kline . |
| 4,286,341 | 9/1981 | Greer et al. . |
| 4,304,010 | 12/1981 | Mano . |
| 4,321,711 | 3/1982 | Mano . |
| 4,355,426 | 10/1982 | MacGregor . |
| 4,550,447 | 11/1985 | Seiler, Jr. et al. . |
| 4,604,762 | 8/1986 | Robinson . |
| 4,623,347 | 11/1986 | Kira . |
| 4,655,771 | 4/1987 | Wallsten . |
| 4,743,252 | 5/1988 | Martin, Jr. et al. ..................... 623/1 |

FOREIGN PATENT DOCUMENTS

| | | |
|---|---|---|
| 1092303 | 12/1980 | Canada .................................. 623/1 |
| 2931 | 7/1979 | European Pat. Off. . |
| 0117072 | 8/1984 | European Pat. Off. . |
| 0130401 | 1/1985 | European Pat. Off. . |
| 3204719 | 9/1982 | Fed. Rep. of Germany . |
| 1265246 | 3/1972 | United Kingdom . |

OTHER PUBLICATIONS

Szycher et al., Synthetic Biomedical Polymers, Concepts and Applications, 1980, pp. 29–38.

Primary Examiner—Alan W. Cannon
Attorney, Agent, or Firm—Armstrong, Nikaido, Marmelstein, Kubovcik & Murray

[57] ABSTRACT

An artificial vessel, wherein the vessel wall is made of an elastomer having a porous structure with pores at any part of the vessel wall from the inner surface to the outer surface and consists of at least 2 concentric layers, each layer having a substantially uniform porosity percentage, the inmost layer having a thickness of from 30 to 500 μm and a porosity percentage of from 95 to 80% and other layers having a lower porosity percentage than that of the inmost layer, and the porosity of the whole vessel wall is from 90 to 75%.

The artificial vessel may also be reinforced with tubular material made of fiber or with heat-set tubular material made of fiber.

The artificial vessel of the present invention has a porosity, a compliance approximate to that of a vital vessel, and a contact surface with blood having an excellent blood compatibility.

3 Claims, 1 Drawing Sheet

ARTIFICIAL VESSEL

CROSS-REFERENCE TO RELATED APPLICATION

This is a continuation-in-part of application Ser. No. 900,052 filed on Aug. 25, 1986, abandoned.

BACKGROUND OF THE INVENTION

The present invention relates to an artificial vessel having a porosity, a compliance approximate to that of a vital vessel, and a contact surface with blood having an excellent blood compatibility. More particularly, the present invention relates to an artificial vessel having a porosity, a compliance approximate to that of a vital vessel, and a contact surface with blood having an excellent blood compatibility.

In recent years, study on the artificial vessel has proceeded with a progress of vascular surgery and many artificial vessels have been developed. Hitherto, for an artificial vessel for artery of a medium- or large-caliber with a diameter of about not less than 6 mm, Debakey artificial vessel made of woven Dacron (USCI. Co., Ltd. of U.S.A.), Gore-Tex (Gore Co., Ltd. of U.S.A.) which is made of an expanded polytetrafluoroethylene (hereinafter referred to as "EPTFE"), and the like have been clinically used.

The above artificial vessels have pores which communicate the inside and the outside of the vessel wall. Soon after the artificial vessel is grafted into a living body, the vessel is covered with pseudointima and the pseudointima grows into the communicating pores, which makes the artificial vessel encapsulated to serve as the artificial vessel. Such property of having the communicating pores suited for encapsulation is hereinafter referred to as "porosity".

However, these artificial vessels have a disadvantage of a poor patency since they have a mechanical property, especially a compliance extremely different from that of a vital vessel and a contact surface with blood having a bad blood compatibility. From this reason, they cannot be clinically used as the artificial vessel for vein or in a vascular reconstructive surgery of artery of a small-caliber with an inner diameter of not more than about 6 mm and autogeneous vein grafts have hitherto been employed in vascular reconstructive surgery of arteries below knees or of coronary artery.

For obtaining the artificial vessel having an excellent patency, especially the artificial vessel suited for application in the vascular reconstructive surgery of arteries of small-caliber, it appears to be important for the artificial vessel to have a mechanical property, especially a compliance approximate to that of a vital vessel and to have a contact surface with blood having an excellent blood compatibility as well as to have a porosity, which improves the patency of the artificial vessel. However, such artificial vessel has hitherto not yet been prepared.

OBJECT OF THE INVENTION

Under the above-mentioned circumstances, the present invention is aimed at providing an artificial vessel with an excellent patency having a porosity, a mechanical property (especially a compliance) approximate to that of a vital vessel, and a contact surface with blood having an excellent blood compatibility, especially the artificial vessel which can also be used as an artificial vessel of small-caliber with an inner diameter of not more than about 6 mm.

SUMMARY OF THE INVENTION

The present invention has been accomplished by finding that an artificial vessel with a porosity, a mechanical property (especially a compliance) approximate to that of a vital vessel and a contact surface with blood having an excellent blood compatibility can be prepared by controlling a porosity percentage of an artificial vessel wherein the vessel wall is made of an elastomer. According to the present invention, there is provided an artificial vessel, wherein the vessel wall is made of an elastomer having a porous structure with pores at any part of the wall from the inner surface to the outer surface and consists of at least 2 concentric layers, each layer having a substantially uniform porosity percentage, the inmost layer having a thickness of from 30 to 500 $\mu$m and a porosity percentage of from 95 to 80% and other layers having a lower porosity percentage than that of the inmost layer, and the porosity of the whole vessel wall is from 90 to 75%.

DETAILED DESCRIPTION

Figure 1:
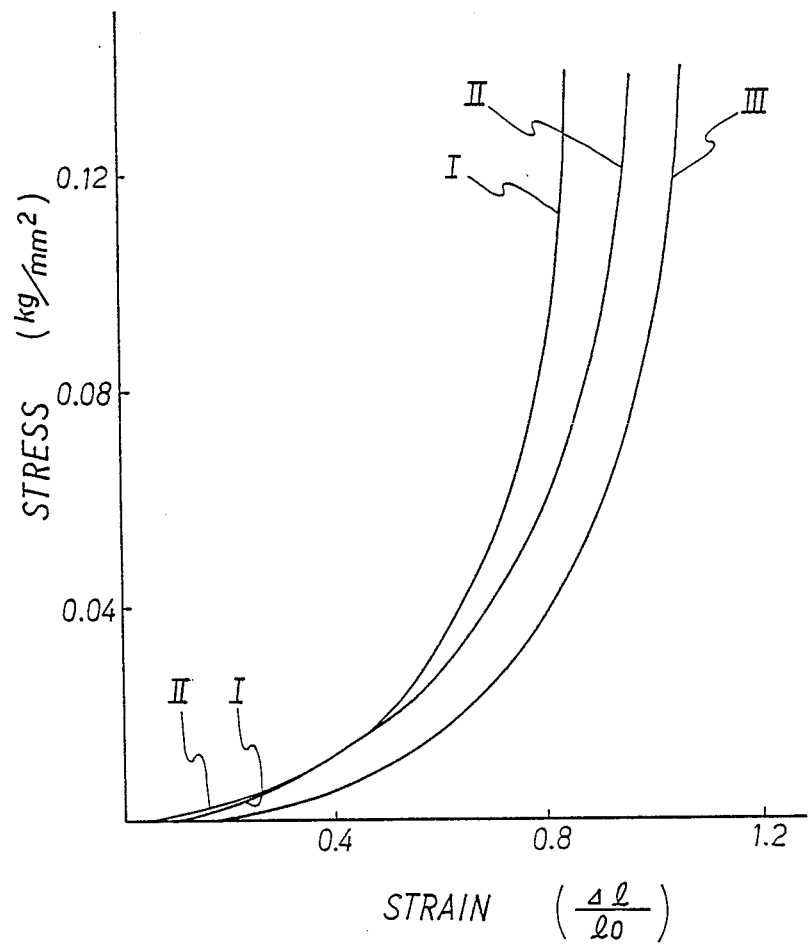
FIG. 1 is a graph of stress-strain curves of carotid artery (curve I), the artificial vessel prepared in Example 3 (curve II) and thoracic aorta (curve III), respectively.

The vessel wall of the artificial vessel of the present invention is made of an elastomer having a porous structure. Such vessel wall made of an elastomer having a porous structure makes the mechanical property, especially the compliance of artificial vessel approximate to that of a vital vessel.

The porous structure of the elastomer contains pores at any part of the vessel wall from the inner surface to the outer surface. The pores are communicated with each other in at least one part thereof and there are openings formed by at least one part of the pores on the inner surface and the outer surface of the vessel wall, thus the artificial vessel has a porosity. A partition which forms the pores is made of the elastomer and connected with each other continuously. Preferably, the partition itself contains a large number of small pores or holes with a maximum diameter of less than 1 $\mu$m so that the vessel wall has a lower density structure and the artificial vessel having a compliance approximate to that of a vital vessel is obtained.

The vessel wall of the artificial vessel of the present invention consists of at least 2 concentric layers. The pore number per unit volume in each layer is substantially uniform at any part of the layer.

Preferably, the pores present at any part of the vessel wall from the inner surface to the outer surface have substantially uniform size.

Since at the vicinity of the inner surface, the outer surface and of the boundary between a layer and another layer of the vessel wall, the pores are slightly small and the vessel wall is comparatively dense, the pore size is not entirely uniform over the layer. However, if such ununiformity does not impair the porosity in each layer, the pores may be considered to be substantially uniform. Although a maximum diameter of a cross section of the pores is not particularly limited, it is preferably 1 to 100 $\mu$m, more preferably 3 to 75 $\mu$m. When the maximum diameter is more than 100 $\mu$m, the strength of the vessel wall is decreased or the porosity becomes too large. When the maximum diameter is less than 1 μm, the porosity becomes poor or the compliance becomes too small.

Although the shape of the openings present on the inner surface and the outer surface of the porous structure is not particularly limited, the shape of the openings present on the inner surface is preferably round or oval. A maximum diameter of such shape is preferably from 1 to 100 μm, more preferably from 5 to 50 μm, and most preferably from 10 to 30 μm. When the maximum diameter is more than 100 μm, a blood flow is disturbed and an antithrombogenisity of the artificial vessel is lowered. When the maximum diameter is less than 1 μm, the encapsulation of the artificial vessel becomes poor.

The porosity percentage of the inmost layer of the vessel wall is from 95 to 80% and the porosity percentage of other layers is lower than that of the inmost layer, and the porosity of the whole vessel wall is from 90 to 75%. Preferably, the porosity percentage of the inmost layer is from 95 to 83%, the porosity percentage of other layers is lower than that of the inmost layer, and the porosity percentage of the whole vessel wall is from 90 to 80%. The thickness of the inmost layer is from 30 to 500 μm, preferably from 50 to 250 μm. It is preferable that the porosity percentage of outer layers is lower than that of the inmost layer by not less than 2.5%.

The term "porosity percentage" in the present invention is defined by the following equation (1).

$$\text{porosity percentage} = \frac{V - \frac{W}{A}}{V} \times 100 \qquad (1)$$

In the above equation (1), V is the vessel wall volume of the artificial vessel, W is the weight of the artificial vessel, and A is a specific gravity of the material forming the artificial vessel. The porosity percentage is determined by the amount of the pores present in the vessel wall and the amount of the small pores or holes present in the partition which forms the pores.

In the artificial vessel of the present invention, the porosity percentage greatly affects the mechanical property, especially the compliance, and the blood compatibility of the contact surface with blood. The porosity percentage has a positive correlation with the compliance, i.e. the compliance increases as the porosity percentage of the whole vessel wall increases. A porosity percentage of more than 90% is not preferable since at this porosity percentage the compliance of the artificial vessel becomes larger than that of a vital vessel. A porosity percentage of less than 75% is not preferable since at this porosity percentage the compliance of artificial vessel becomes smaller than that of a vital vessel.

The porosity percentage of the inmost layer of the artificial vessel is nearly in proportion to the number of the pores present on the inner surface, i.e. the contact surface with blood, of the artificial vessel. Further, the more the number of the pores present at the contact surface with blood increases, the more the patency of the artificial vessel is improved with the preferable encapsulation and the excellent blood compatibility. When the porosity percentage of the inmost layer of the artificial vessel is less than 80%, the blood compatibility tends to become poor. Therefore, in order to control the mechanical property, especially the compliance, and the number of the pores present on the contact surface with blood by controlling the porosity percentage, it is advantageous that the number of the pores present on the contact surface with blood is increased by increasing the porosity percentage of the inmost layer of the vessel wall, and the mechanical property, especially the compliance, is controlled by lowering the porosity percentage of the outer layers of the vessel. Also, when the porosity percentage of the inmost layer of the artificial vessel is more than 95%, the shape of openings on the contact surface with blood becomes so irregular that the blood compatibility becomes poor and that the strength of contact surface becomes too weak.

The elastomer used in the present invention is a thermoplastic elastomer having an excellent antithrombogenicity which does not release any low molecular compound, which causes acute poisoning, inflammation, hemolysis, fever and the like, and does not seriously impair the physiologic function of blood. Examples of such elastomers are, for instance, polystyrene elastomers, polyurethane elastomers, polyolefin elastomers, polyester elastomers, and the like. The above elastomers can be used in a single form or as a mixture thereof.

Since the characteristics as an elastomer is required only after the elastomer is formed into the artificial vessel, even a mixture of the above elastomer with a polymer not having characteristics of the elastomer can be used as the elastomer in the present invention insofar as the final product has characteristics as an elastomer.

Among the above elastomers, a thermoplastic polyether type segmented polyurethane, including segmented polyurethane urea, hereinafter the same, elastomers are more preferable in viewpoint of strength, elongation, durability, antithrombogenisity, processability and the like. A segmented polyurethane containing fluorine atom in a hard segment or a soft segment, and a segmented polyurethane disclosed in Japanese Unexamined Patent Publication (KOKAI) No. 211358/1982, which contains polydimethylsiloxane in its main chain are still more preferable. Particularly preferable elastomers are a segmented polyurethane which contains, in a part of a soft segment, polydimethylsiloxane having the formula:

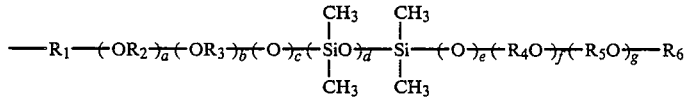

wherein $R_1$, $R_2$, $R_3$, $R_4$, $R_5$ and $R_6$ are an alkylene group having at least 1 carbon atom, preferably an alkylene group having 2 to 6 carbon atoms such as ethylene, propylene, butylene or hexamethylene; a and g are 0 or an integer of 1 to 30, b, c, e and f are 0 or 1, and d is an integer of not less than 2, preferably from 5 to 135.

As mentioned above, the artificial vessel of the present invention has an excellent patency because of the porosity, the compliance approximate to that of a vital vessel, and the excellent blood compatibility of the contact surface with blood. However, in order to prevent a rupture or an impairment which may occur due to an abnormally high pressure in process of surgery and the like, or to maintain a durability for a long period, the artificial vessel is preferably reinforced with tubular material made of fiber. Further, the artificial vessel is preferable reinforced with tubular material made of fiber so as to have a stress-strain curve approximate to that of a vital vessel.

Although the artificial vessel reinforced with tubular material made of fiber can be subjected to a sterilization procedure by gamma ray or ethylene oxide, it has a problem of shrinking in a sterilization procedure by boiling or by high-pressure steam. Therefore, in order to obtain the artificial vessel which does not shrink even in the sterilization procedure by boiling or by high-pressure steam, the artificial vessel is preferably reinforced with heat-set tubular material made of fiber.

The "heat-set" treatment in the present invention is to heat the tubular material made of fiber to such a degree that the tubular material does not shrink in the sterilization procedure by boiling or by high-pressure steam, for example, at 121° C. for 20 minutes. In practice, the heat-set treatment can be carried out by boiling, by exposing to steam, by maintaining a high temperature atmosphere, by conducting the same procedure as sterilization by high-pressure steam, or the like. Among the above procedures, the sterilization procedure by high-pressure steam, by which the heat-set treatment is surely achieved with a good operatability, is preferable.

The heat-set tubular material made of fiber in the present invention may be any of those prepared by heat-setting a fiber and then forming the fiber into a tubular material, by heat-setting a fiber, forming the fiber into a tubular material and further heat-setting the obtained tubular material, or by heat-setting a tubular material made of fiber. In viewpoint of operability, the heat-set tubular material made of fiber is preferably prepared by heat-setting a tubular material made of fiber.

The artificial vessel reinforced with the heat-set tubular material made of fiber in the present invention is an artificial vessel where at least a part of the tubular material is in contact with and/or is combined with the porous material made of elastomer, and a mechanical interaction exists between the tubular material and the porous material made of elastomer in such a degree that both the tubular material and the porous material show nearly the same strain against blood pressure or stress from the outside.

The fiber used in the present invention is a fine and long fiber having a length not less than 100 times longer than its diameter, which is usually employed for producing a yarn, a net yarn, a rope, a woven fabric, a knitting fabric, a braid, a nonwoven fabric, or the like. The fiber may be made of an organic material or of an inorganic material, insofar as the fiber does not give any bad influence to a living body, deterioration of the fiber in a living body is negligible, and the fiber is stable in the sterilization procedure, and also the fiber can be formed into the tubular material. From viewpoints of processability, commercial availability, pliability and uniformity, there are preferably employed a regenerated man-made fiber, a semi-synthetic fiber and a synthetic fiber. Examples of the fiber are, for instance, cellulose fibers, protein fibers, polyamide fibers, polyester fibers, polyurethane fibers, polyethylene fibers, polystyrene fibers, polyvinylchloride fibers, polyvinylidene chloride fibers, polyfluoroethylene fibers, polyacrylic fibers, polyvinyl alcohol fibers and the like. Among them, a fiber having a stretching property is more preferably employed. Examples of such stretch fibers are, for instance, fibers originally having a self-stretching property such as rubber fibers, polyurethane elastic fibers or polyester elastic fibers; fibers which acquire the stretching property after a processing such as stretch bulked processed fibers, covered yarns, fancy yarns, bulky yarns, A to Z yarns and conjugate fibers; and the like.

The tubular material made of fiber used in the present invention is a tubular material made of the above-mentioned fiber; a yarn spun from at least one of the above-mentioned fibers; a multifilament of at least one of the above-mentioned fibers; a woven fabric, a knitting fabric, a braid, a nonwoven fabric or a fabric combined thereof, which are produced from the above fiber, yarn or multifiber, and the like. A tubular material made of a polyurethane foam of sponge like structure can also be employed.

The tubular material made of fiber is preferably used so that the artificial vessel, when the tubular material and the porous structure are combined together, has a compliance approximate to that of a vital vessel and further a stress-strain curve approximate to that of a vital vessel. Such properties of the tubular material can be achieved by, for instance, either of the following two processes or a combination thereof. One process is to control the number of the connecting or contacting points of the fibers or yarns and to loosen the connecting point of the fibers or yarns. Another process is to use a stretch fiber.

The tubular material may be formed by fiber or material made of fiber by itself or by combining the fiber with the porous material made of elastomer so that the tubular structure is formed at the finishing. In viewpoints of processability, workability and establishment of the stress-strain curve approximate to that of a vital vessel, there is preferably employed a tubular material made of knitting fabric of the fiber, more preferably a tubular material made of knitting fabric of stretch fiber.

In order to obtain the stress-strain curve approximate to that of a vital vessel, there are preferably employed, among the stretch fibers, stretch bulked processed fibers such as Woolie nylon and Woolie tetron, covered yarns which are prepared by winding another spun yarn or filament on the attached rubber or spandex filament, and the like.

Although a stress-strain curve of a vital vessel cannot be generally determined since it varies with the kind of the vessel, e.g. artery or vein, the diameter of the vessel and the like, a vital vessel substantially has the stress-strain curve (I) or (III) as shown in FIG. 1. The curves (I) and (III) are stress-strain curves of carotid artery and of thoracic aorta, respectively. These stress-strain curves show that an elastic modulus, which is low at a normal blood pressure level, increases drastically when a stress over the normal blood pressure level is applied. As shown in FIG. 1, the stress-strain curve (II) of the artificial vessel of the present invention approximates to those of a vital vessel. The stress-strain curve can be measured with a tension testing machine usually employed in the polymer material field such as, for instance, Autograph AG-2000 A made by Shimazu Coorporation.

The "compliance" as used herein is defined by the equation (2):

$$C = \frac{\Delta V}{V_o \cdot \Delta P} \times 100 \quad (2)$$

wherein C is a compliance, Vo is a volume of a measured vessel at the inner pressure of 50 mmHg, $\Delta P$ is a pressure difference of the inner pressure, i.e. 100 mmHg of difference between 50 and 150 mmHg, $\Delta V$ is a volume increased of the vessel when the inner pressure rises from 50 mmHg to 150 mmHg. In the practical measurement, a vessel is inserted into a closed circuit, and a volume of an injected liquid and a pressure variation in the circuit are measured by means of a micro-analysis pump. From the results, the compliance can be calculated according to the above equation (2).

In case of the measurement of the artificial vessel having the porosity, the communicating pores in the vessel wall are plugged by a procedure such as pre-clotting.

The compliance of a vital vessel varies with the kind of a vital vessel, e.g. artery or vein, the diameter of the vessel and the like. Therefore, although a preferable compliance for the artificial vessel cannot be generally determined since it varies with the diameter of the artificial vessel, the region to which the artificial vessel is applied, and the like, the artificial vessel of the present invention is prepared so as to have a compliance approximate to that of each vital vessel, for example, the compliance of from 0.1 to 0.8. For arteries of a small-caliber, the artificial vessel preferably has a compliance of from 0.1 to 0.5.

A process for preparing the artificial vessel of the present invention is explained in the following description.

The artificial vessel of the present invention can be prepared by repeating one or two times a procedure of coating an elastomer solution containing a pore-forming agent and/or having a cloud point on a mandrel and then immersing the coated mandrel into a coagulating liquid. The porosity percentage can be controlled by the particle size and the amount of the pore-forming agent, the solvent composition of the elastomer solution, the kind of the coagulating liquid and the like. In order to obtain the artificial vessel with the increased porosity percentage at the inner portion of the vessel wall, the above conditions are suitably controlled at the procedure of preparing the inner portion of the vessel wall.

When the artificial vessel is reinforced with the tubular material made of fiber, the tubular material made of fiber is made to be present on the mandrel at any step of the above procedure.

The elastomer solution used in the present invention is classified into ① an elastomer solution containing a pore-forming agent, ② an elastomer solution having a cloud point and ③ an elastomer solution containing a pore-forming agent and having a cloud point.

The elastomer solution containing a pore-forming agent ① essentially comprises a pore-forming agent, the elastomer and a solvent in which the elastomer dissolves (hereinafter referred to as "good solvent") in which the pore-forming agent is uniformly dispersed. The preferable amount of the pore-forming agent is from 1 to 250% (percentage of the volume of the pore-forming agent/the volume of the elastomer, hereinafter the same), more preferably from 20 to 200%, and most preferably from 50 to 150%. When the elastomer solution is dipped into the coagulating liquid, the elastomer is deposited due to replacement of the good solvent with the coagulating liquid. The pore-forming agent in the deposited elastomer is dissolved and removed to give the porous structure of the artificial vessel of the present invention. If necessary, for controlling the coagulation rate of the elastomer solution and a density or shape of the porous structure, a solvent in which the elastomer does not dissolve but miscible with the good solvent (hereinafter referred to as "poor solvent") may be added.

The elastomer solution having a cloud point ② essentially comprises the elastomer, the good solvent and the poor solvent. The poor solvent is employed in such an amount that the solution has a cloud point. The term "cloud point" means a temperature at which a dissolved polymer in a solution is deposited in a form of colloid, in other word, a temperature at which phase change occurs. When the elastomer solution ② is handled at a temperature below the cloud point, it is difficult to form a uniform coating of the elastomer solution, and thus a proper porous structure cannot be obtained. Therefore, it is preferable to coat the mandrel with the elastomer solution at a temperature above the cloud point, and then immediately or after the phase change, to immerse the coated elastomer solution into the coagulating liquid of a temperature below the cloud point. According to the procedure, the porous structure can be formed by changing the phase of the elastomer solution in the coating layer and depositing the elastomer in the coagulating liquid in the above order or at the same time.

The elastomer solution containing a pore-forming agent and having a cloud point ③ essentially comprises the elastomer, the pore-forming agent, the good solvent and the poor solvent, the amount of the poor solvent being such an amount that the solution has a cloud point. From the elastomer solution ③, the porous structure can be formed by depositing the elastomer and then dissolving to remove the pore-forming agent as in the case of the elastomer solution ②.

The pore-forming agent used in the present invention is insoluble in the good solvent and can be removed from the prepared artificial vessel. The particle size of the pore-forming agent is preferably from 1 to 100 $\mu$m, more preferably from 10 to 74 $\mu$m, and most preferably from 20 to 50 $\mu$m. Examples of the pore-forming agent are, for instance, calcium carbonate, glucose, starch, casein, collagen, gelatin, albumin and the like.

The good solvent used in the present invention varies depending on the kind of the elastomer and is not particularly limited. Examples of the good solvent are, in case of the polyurethane elastomers, for instance, N,N-dimethylacetamide, N,N-dimethylformamide, N-methyl-2-pyrrolidone, dioxane, tetrahydrofuran, a mixture thereof, and the like.

As the poor solvent used in the present invention, there can be employed any solvent in which the elastomer does not dissolve, but miscible with the good solvent. Examples of the poor solvent are, for instance, water, lower alcohols, ethylene glycol, propylene glycol, 1,4-butane diol, glycerine, a mixture thereof, and the like.

The coagulating liquid used in the present invention may be substantially the same as the poor solvent. Examples of the coagulating liquid are, for instance, water, lower alcohols, ethylene glycol, propylene glycol, 1,4-butane diol, glycerin, a mixture thereof, and the like.

The mandrel used in the present invention is not particularly limited insofar as the mandrel is not dissolved in the elastomer solution. Preferable mandrel is a rod having a smooth surface such as a glass rod, a Teflon rod or a stainless steel rod. When using dies having various shapes instead of the rod, various medical articles other than the above tubular article can be obtained. For instance, if a plate is used as the die, there can be provided a film-like article which can be utilized for an artificial skin.

The tubular material made of fiber is made to be present on the mandrel by, for instance, covering the mandrel with the tubular material made of fiber or by winding fiber or a strip made of fiber on the mandrel to form a tubular structure. The tubular material made of fiber may be made to be present on the mandrel directly, or on the mandrel on which the elastomer is deposited. It is preferable that the tubular material made of fiber is made to be present on the mandrel on which the elastomer is deposited, followed by repeating one or two times a procedure of coating the elastomer solution and of depositing the elastomer.

The artificial vessel prepared by the above procedures has the following excellent properties.

① The artificial vessel has a porosity useful for encapsulation of the vessel.

② The artificial vessel has the contact surface with blood having an excellent blood compatibility.

③ The artificial vessel has a compliance approximate to that of a vital vessel.

In case of the artificial vessel reinforced with the tubular material made of fiber, the vessel has a high strength and durability and a stress-strain curve of the vessel approximate to that of a vital vessel. In case of the artificial vessel reinforced with the heat-set tubular material made of fiber, the vessel can be subjected to the sterilization procedure by boiling or by high-pressure steam.

In addition, the artificial vessel of the present invention has the following useful properties, since the vessel wall of the artificial vessel is made of the elastomer having the porous structure and the vessel can be reinforced, as occasion demands, with the tubular material made of fiber.

④ A surgical needle easily penetrates to the artificial vessel, and thus the vessel is easily sutured.

⑤ A bore formed by a needle can be closed by itself.

6. A kinking is hardly formed in the practical use where blood pressure is applied.

⑦ The artificial vessel has a high durability.

The artificial vessel of the present invention having the above-mentioned properties has an excellent patency and a good operability in the vascular reconstruction surgery.

Therefore, the artificial vessel of the present invention can be used as an artificial vessel, an artificial vessel for by-pass, a material for patch, in the vascular reconstructive surgery of a vital vessel, moreover, a blood access. Especially, the artificial vessel of the present invention is preferably used as an artificial vessel for artery having a compliance of from 0.1 to 0.8. Also, the artificial vessel of the present invention can be used as an artificial vessel of small-caliber for artery having the inner diameter of from about 1 to about 6 mm and a compliance of from 0.1 to 0.5, which has not hitherto been available in clinical use. Thus, the artificial vessel of the present invention is preferably used for the artificial vessel in vascular reconstructive surgery of arteries below knees and for the artificial vessel for by-pass between aorta and coronary. In addition, the artificial vessel of the present invention can also be used as an artificial tube for a soft vital tube such as an ureter.

The present invention is more particularly described and explained by means of the following Examples. It is to be understood that the present invention is not limited to the Examples and various changes and modifications may be made without departing from the scope of the present invention.

EXAMPLE 1

After synthesizing a pre-polymer with 27.35 parts (parts by weight, hereinafter the same) of 4,4'-diphenylmethane diisocyanate and 54.7 parts of polyoxytetramethylene glycol (molecular weight: 2000), the pre-polymer chain was extended with 4.75 parts of ethylene glycol and 13.2 parts of polydimethylsiloxane having polyethylene glycol at the both ends (average molecular weight of polyethylene glycol at the both ends: 681, average molecular weight of polydimethylsiloxane: 1040) to give a segmented polyurethane containing polydimethylsiloxane in the main chain.

The thus obtained polyurethane had a tensile strength of 350 kg/cm$^2$, an elongation of 670% and a critical surface tension calculated from Zisman plot of 28 dyn/cm.

Into a mixed solvent of 60 ml of dioxane and 30 ml of N,N-dimethylacetamide, 15 g of casein having a particle size of not more than 30 $\mu$m was dispersed with stirring by a homogenizer and thereto 10 g of the above polyurethane was added to dissolve with stirring. A glass lod having a diameter of 3 mm was immersed into the dispersion liquid and then taken out to coat the dispersion liquid on the glass rod, which was then immersed into ethylene glycol to deposit the elastomer.

The porosity percentage in the inmost layer of a thickness of about 100 $\mu$m of the artificial vessel was measured at this stage as will be mentioned hereinafter.

The above procedure was further repeated three times employing the same dispersion liquid having the same composition as above except for using 10 g of casein. After sufficiently depositing the elastomer, the obtained material was washed with water and the glass rod was pulled out to give a tubular material, which was immersed into an aqueous solution of sodium hydroxide at pH 13.5 to remove casein with extraction and then washed with water sufficiently to give an artificial vessel.

The obtained artificial vessel had an inner diameter of about 3 mm and an outer diameter of about 4.1 mm. From an observation with a scanning type electron microscope, there were many circular or oval openings of pores having a diameter of about 20 $\mu$m on the inner surface of the vessel wall and openings of pores with a round or indefinite shape having a diameter of from about 1 to about 10 $\mu$m on the outer surface of the vessel wall. A cross section of the vessel wall had a network structure.

By calculating the porosity percentage of the artificial vessel from the equation (1), it proved that the artificial vessel had the porosity percentage of about 88% in the inmost layer of a thickness of about 100 $\mu$m and of 84% as a whole.

Then, water was passed through the vessel wall at a pressure of 120 mmHg, and it was observed that about 50 ml/min. of water soaked through to the outside per 1 cm$^2$ of the inner surface. Thus the artificial vessel was proved to have porosity.

After pre-clotting blood of bovine in the vessel and cutting the pre-clotted vessel to 8 cm, the artificial vessel was inserted into a closed circuit. The ACD blood of bovine was fed into the closed circuit by a quantitative pump which feed 0.05 ml per stroke, and the change of the inner pressure was measured. The compliance proved to be 0.4 from calculation according to the equation (2) on the basis of the number of strokes and the chage of the inner pressure.

The artificial vessel of about 7 cm length was grafted to a femoral artery of an adult mongrel dog. The grafted vessel showed a patency for not less than two months.

The artificial vessel did not fray when cutting at any point, and had an excellent property in suturing. In addition, the bores of the surgical needle were closed by themselves when the needle was removed. Further, the vessel tended not to form a kinking under an inner pressure of from 50 to 150 mmHg.

From the above obtained results, it is clear that the artificial vessel has excellent properties as an artificial vessel of small-caliber for artery.

EXAMPLE 2

Before the last procedure of immersing the glass rod into the dispersion liquid in Example 1, a tubular material having a diameter of about 4 mm prepared by knitting covered yarn, which was prepared by winding tetron fiber of 30 deniers on spandex of 10 deniers, with a ribbon knitting machine of 24 needle was covered on the glass rod coated with the deposited elastomer. The procedure in Example 1 was repeated other than the above procedure to prepare an artificial vessel reinforced with the tubular material made of fiber.

The obtained artificial vessel had an inner diameter of 3 mm and an outer diameter of about 4.5 mm. The porosity percentage calculated from the equation (1) was 88% in the inmost layer having a thickness of about 100 $\mu$m, and 85% as a whole.

The obtained artificial vessel was observed as in Example 1 to prove that it had the same contact surface with blood as the artificial vessel prepared in Example 1. A compliance and a penetration volume of water measured as in Example 1 were 0.3 and about 40 ml, respectively.

By using Shimazu Autograph AG 2000A, a stress-strain curve was measured. The artificial vessel had a stress-strain curve approximate to that of a vital vessel.

A patency of the artificial vessel was measured as in Example 1 and proved to be not less than two months.

EXAMPLE 3

A dispersion liquid was prepared by adding 117 ml of N,N-dimethylacetamide and 117 ml of dioxane to a mixture of 32 g of polyurethane as in Example 1 and 48 g of casein having a particle size of from 30 $\mu$m to 40 $\mu$m with stirring. A glass rod was immersed into the dispersion liquid and then taken out to coat the dispersion liquid on the glass rod uniformly. The coated glass rod was immersed into an aqueous solution containing 30% by volume of dioxane to deposit the elastomer.

The above procedure was repeated once more using a dispersion liquid having the same composition as above except for using each 27 g of polyurethane and of casein.

A tubular material prepared by knitting Woolie polyester fiber of 50 deniers with a ribbon knitting machine of 24 needle was sterilized by high-pressure steam at 121° C. for 20 minutes and then dried. The thus obtained tubular material having a diameter of about 4 mm was covered on the glass rod having the deposited elastomer. The glass rod covered with the tubular material was immersed into a dispersion liquid having the same composition as above except for using each 8.5 g of polyurethane and of casein, and then taken out to deposit the elastomer. Thereafter, the procedure as in Example 1 was repeated to give an artificial vessel.

The obtained artificial vessel had an inner diameter of 3 mm and an outer diameter of about 4.2 mm. The porosity percentage was 87% in the inmost layer having a thickness of about 300 $\mu$m, and 84% as a whole.

A compliance and a penetration volume measured as in Example 1 were 0.45 and about 70 ml/cm$^2$, respectively. A stress-strain curve measured with Shimazu Autograph AG-2000A was shown in FIG. 1, which was approximate to that of a vital vessel.

The artificial vessel was sterilized by high-pressure steam at 121° C. for 20 minutes without any change in shape or size, which showed that the artificial vessel can be subjected to the sterilization procedure by high-pressure steam.

The patency of the artificial vessel was measured as in Example 1 and proved to be not less than two months.

What I claim is:

1. An artificial vessel consisting essentially of a porous vessel wall which contains pores throughout the thickness of the vessel wall from the inner surface of the vessel wall to the outer surface of the vessel wall, said vessel wall consisting essentially of concentric layers of porous thermoplastic elastomeric material, wherein each layer of porous elastomeric material has a substantially uniform porosity percentage, the innermost elastomeric layer has a thickness of 30 to 500$\mu$ and a porosity percentage of 95 to 80%, the remaining elastomeric layers have a lower porosity percentage than the innermost elastomeric layer, and the overall porosity percentage of the elastomeric layers is 90 to 75%.

2. The artificial vessel of claim 1, wherein the compliance of the vessel wall is from 0.1 to 0.8.

3. The artificial vessel of claim 1, wherein the porous thermoplastic elastomeric material is a segmented polyurethane.

* * * * *